United States Patent [19]

Der Kinderen

[11] Patent Number: 4,718,269
[45] Date of Patent: Jan. 12, 1988

[54] SYSTEM FOR MEASURING PARTICLE TRANSPORT IN A FLUID

[75] Inventor: Wilhelmus J. G. J. Der Kinderen, Delft, Netherlands

[73] Assignee: Sticting "Stichting Waterbouwkundig Laboratorium", Delft, Netherlands

[21] Appl. No.: 748,779

[22] Filed: Jun. 25, 1985

[51] Int. Cl.$^4$ .......................... G01N 29/02; G01F 1/66
[52] U.S. Cl. ........................................ 73/28; 73/61 R; 73/861.25
[58] Field of Search .................. 73/61 R, 189, 861.25, 73/432 P, 432 S, 24, 28; 343/8; 356/28, 336, 338, 339, 392, 343

[56] References Cited

U.S. PATENT DOCUMENTS 3,741,014 6/1973 Tamura ............................ 73/861.25
3,889,533 6/1975 Balser ............................ 73/861.25 X
4,527,420 7/1985 Foote ........................... 73/432 P S X Primary Examiner—Herbert Goldstein
Attorney, Agent, or Firm—Rosen, Dainow & Jacobs

[57] ABSTRACT

System for measuring particle transport in a fluid, comprising a transmitter for transmitting a wave beam in the direction of a measuring volume in the fluid under the control of an electrical control signal and a receiver receiving, within a reception beam, waves scattered by particles in said measuring volume and supplying a corresponding electrical reception signal. The measuring volume is determined by the intersection of the transmission beam and the reception beam, The system comprises a second receiver which receives scattered waves from a second correspondingly defined measuring volume. The wave propagation path between the transmitter and the second receiver is equal to n times the wave propagation path between the transmitter and the first receiver. A measuring apparatus receives the control signal of the transmitter and the reception signals of both receivers to derive therefrom data relating to the concentration of the particles in the measuring volume and/or the velocity component in the plane of the transmitting and receiving direction of both transducers.

14 Claims, 10 Drawing Figures

SYSTEM FOR MEASURING PARTICLE TRANSPORT IN A FLUID

The invention relates to a system for measuring particle transport in a fluid, comprising a transmitter for transmitting a wave beam in the direction of a measuring volume in the fluid and under the control of an electrical control signal and a receiver for receiving, within a reception beam, waves scattered by particles in said measuring volume and supplying a corresponding electrical reception signal, whereby the measuring volume is determined by the intersection of the transmission beam and the reception beam, and a measuring apparatus to which the control signal of the transmitter and the reception signal of the receiver are supplied to derive from the product signal of said signals data relating to the concentration of the particles in said measuring volume and/or the velocity component in the plane of the transmitting and receiving direction of both transducers.

A system of this type, functioning with acoustical waves and electro-acoustical transducers as transmitters and receivers is described in "The in situ measurements of sediment transport by means of ultrasound scattering" by R. H. J. Jansen, Publ. No. 203, July 1978 of the Waterloopkundig Laboratorium in Delft (Delft Hydraulics Laboratory). Said known system is, for instance, used for measuring the sediment transport in coastal waters. Hereafter said known system as well as the operation thereof will be discussed briefly with reference to FIG. 1.

The transport of sediment particles T is defined as the product of the mass concentration C and the velocity v of the particles. In order to ensure that as little information as possible is lost C and v must be measured continuously, instantaneously and simultaneously. The transducers T1 and T2 illustrated in FIG. 1 are identical piezo-electrical ceramic discs. The area where the narrow transmitting beam and receiving beam intersect each other is the effective measuring volume V. The influence of eventual side lobes may be neglected in practice. The particles which are in the measuring volume will scatter the acoustical waves and part of the scattered energy will be received by the receiving transducer. The electrical signal at the output of said receiving transducer contains information both on the displacement velocity v and on the concentration C of the particles in the fluid. When the particles are moving, due to the Doppler effect a frequency difference is observed between the frequencies f and f' of the transmission signal and the receiving signal, respectively. Said frequency difference forms a measure for the velocity component along the bisector of the angle between the transmission beam and the reception beam. Said velocity component can be written as:

$$v_1 = |v|\cos\sigma = \frac{cf_d}{2f \cdot \cos\phi/2} \quad (1)$$

wherein
$v_1$ = the velocity component along the bisector of the angle between the transmission beam and the reception beam
$|v|$ = modulus of the velocity vector
$\theta$ = angle between the velocity vector and the bisector
$\phi$ = angle between transmission and reception beam
$f_d$ = frequency difference
$c$ = sound velocity.

The concentration C of the particles in the measuring volume can be derived from the signal intensity according to the formula:

$$S^2 = (k_1/m)C_1 \exp -m(k_2C_2+\alpha) \quad (2)$$

in which
$S^2$ = signal intensity of the received signal
m = propagation path length between transmitter and receiver
$C_1$ = concentration in the measuring volume
$C_2$ = concentration along the propagation
$\alpha$ = absorption coefficient of the medium
$k_1$ = constant determined by the transducer and particle characteristics and by the transmitting power
$k_2$ = constant determined by particle characteristics.

Formula (2) is the product of two terms: a linear term, determined by the scattering in the measuring volume, and an exponential term, resulting from extinction of the sound waves in the propagation path m. Said extinction is caused by scattering and absorption by particles and absorption by the fluid itself. Said extinction term causes the non-linearity of the relation between the concentration and the signal intensity and makes this relation ambiguous for higher concentrations. Furthermore, because of the absorption coefficient $\alpha$ the signal intensity is dependent on the temperature and on further characteristics of the fluid in which the particles are moving. When measuring the transport of sand particles in seawater the salinity of the seawater, for instance, plays a role. Also the presence of mud will be expressed through said term.

One has tried already to eliminate the influence of this exponential term by using a third receiving transducer, located within the transmitting beam of the transmitting transducer at such a distance thereof that the length of the sound propagation path between the transmitting transducer and said third transducent is equal to the length of the propagation path between the transmitting transducer and the already present receiving transducer. It appeared, however, that this way of approaching the problem had a number of serious disadvantages. By reflection of sound waves from the surface of the second receiving transducer, two effects appear:

(1) The reflected waves interfere with the incoming waves and if an integer number of half wavelengths "fits" between both transducers, then a standing wave will be generated. It appeared that this process is very temperature dependent. A temperature variation of 0.2° C. results in an amplitude variation of ±10%, which implies a variation of 20% in the concentration determined on the basis thereof.

(2) Because of the reflection, the second receiving transducer functions as jamming transmitter for the velocity measurement. That is, not only does the velocity component along the bisector of the angle between the transmission beam and the reception beam of the second receiving transducer result in a Doppler shift, but furthermore there is a velocity component along the bisector of the angle between the jamming transmitting beam from the third transducer and the reception beam of the second receiving transducer.

A further objection to this approach to attacking the problem is the very unfavourable geometry of the measuring configuration in connection with the hydrodynamical disturbance of the fluid flow in the measuring volume.

An object of the invention is now to indicate in which way an extinction correction can be realized in said known system, i.e., in which way the influence of the exponential term in the above-indicated formula (2) can be eliminated without introducing further serious disadvantages in the system.

In agreement with said object, the system for measuring particle transport in a fluid is, according to the invention, characterized in that the system comprises a second receiver which receives scattered waves from a transmission beam of the transmitter and the reception beam of the first receiver, and supplies a corresponding second reception signal to the measuring apparatus, whereby the wave propagation path between the transmitter and the second receiver is equal to n times the wave propagation path between the transmitter and the first receiver, and the measuring apparatus comprises means for raising the reception signal of the first receiver to the n-th power.

The advantages of the system according to the invention, possible embodiments of said system and further detailed information will be given in the following part of the description with reference to the attached drawings.

Figure 1:
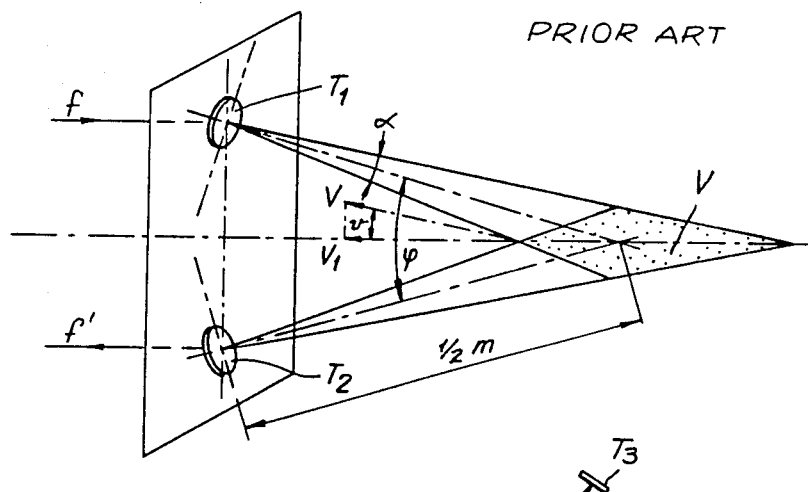
FIG. 1 illustrates the already discussed prior art system.

The prior art circuit, which is already discussed above, is illustrated in FIG. 1. For further details about the operation of this known circuit, reference is made to the publication mentioned above.

FIG. 2 illustrates the basic principle of a system according to the invention. This system comprises three electro-acoustical transducers: the transmitting transducer T1 and the receiving transducers T2 and T3. As shown in FIG. 2, the above-described measuring operation is carried out twice, namely for waves which travel from T1 along the path $m_1$ and arrive at the receiving transducer T2 and waves which travel from the transmitting transducer T1 along the path $m_2$ and arrive at the receiving transducer T3.

The signal intensity $S^2$ of the signal of both transducers T2 and T3 is expressed by the above formula (2):

$$S_1^2 = (k_1/m_1)C_1 \exp -m(k_2C_2+a) \quad (3)$$

$$S_2^2 = (k_3/m_2)C_3 \exp -m(k_4C_4+a) \quad (3)$$

If the concentration C of the particles in the fluid is considered homogeneous, then $C=C_1=C_2=C_3=C_4$ and $k_2=k_4$, and therefore the ratio of $S_1^2$ raised to the n-th power and $S_2^2$ can be expressed as:

$$\frac{(S_1^2)^n}{S_2^2} = \frac{k_1^n C^{n-1} m_2}{k_3 m_1^n} \exp -(nm_1 - m_2)(k_2 C + a) \quad (5)$$

In case the length of the path $m_2$ is selected equal to n times $m_1$:

$$m_2 = n.m_1, \quad (6)$$

then the formula (5) can be simplified into:

$$(S_1^2)^n/S_2^2 = kC^{n-1} \text{ with } k=(k_1^n/k_3m_1)(n/n-1) \quad (7)$$

The result is an elimination of the exponential term in formula (2). Preferably n is selected such that n=2, in which case a linear dependency of the concentration is obtained with a proportionality factor which is determined by:
the transmission power
the characteristics of the transducers
the difference in sound path length In FIG. 2a the signal S1 at the output of the transducer T2 is squared in the multiplier 1. The signal S2 at the output of the receiving transducer T3 is squared in the multiplier 2. The output signals of both multipliers 1 and 2 are divided in the divider 3 resulting in an output signal $S_1^2/S_2^2$. This signal is multiplied in the multiplier 4 by the output signal of multiplier 1, resulting in an output signal from multiplier 4 which, in correspondence with the above-indicated formula (7), whereby n=2, is proportional to the concentration C.

Figure 3:
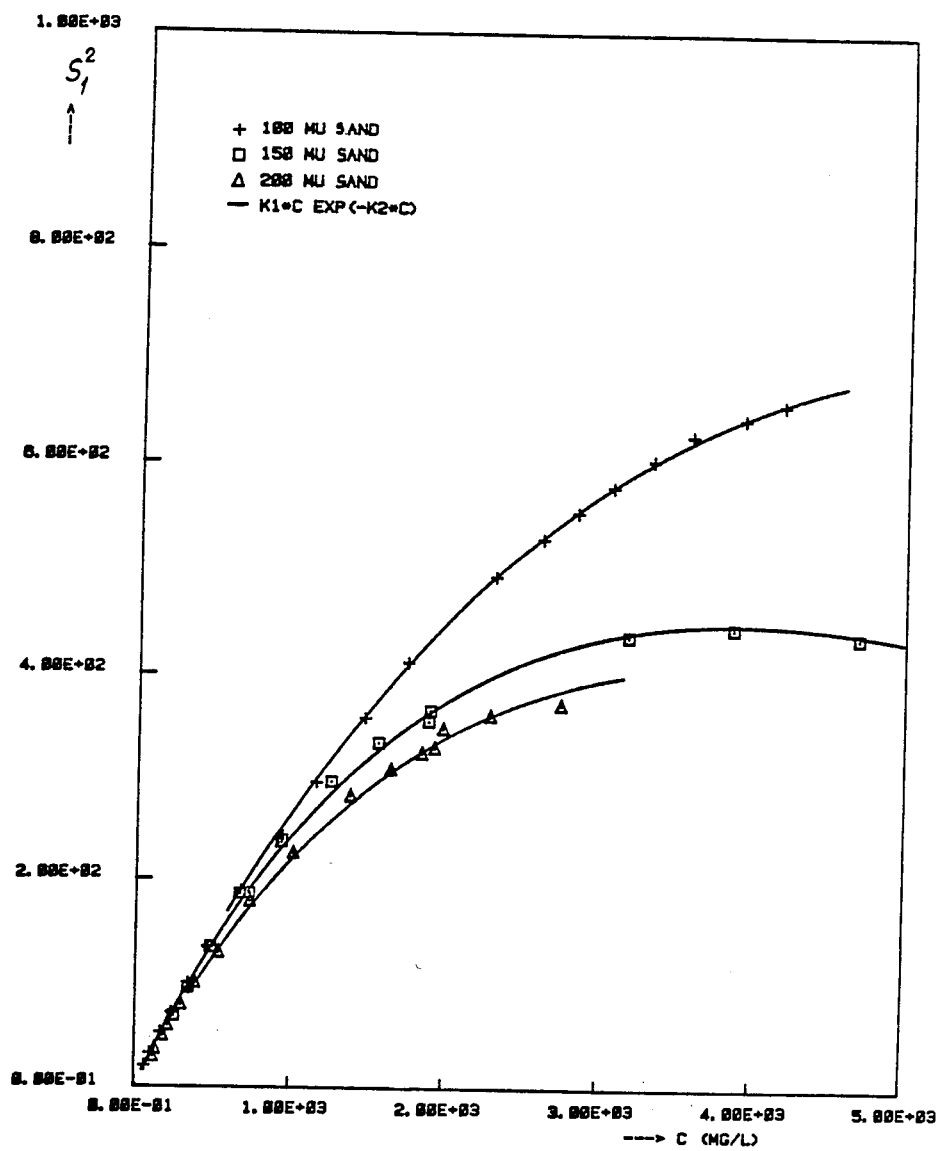
FIG. 3 illustrates in a graphical way the relation between the squared output signal of the second transducer and the particle concentration for various particle sizes.
Figure 4:
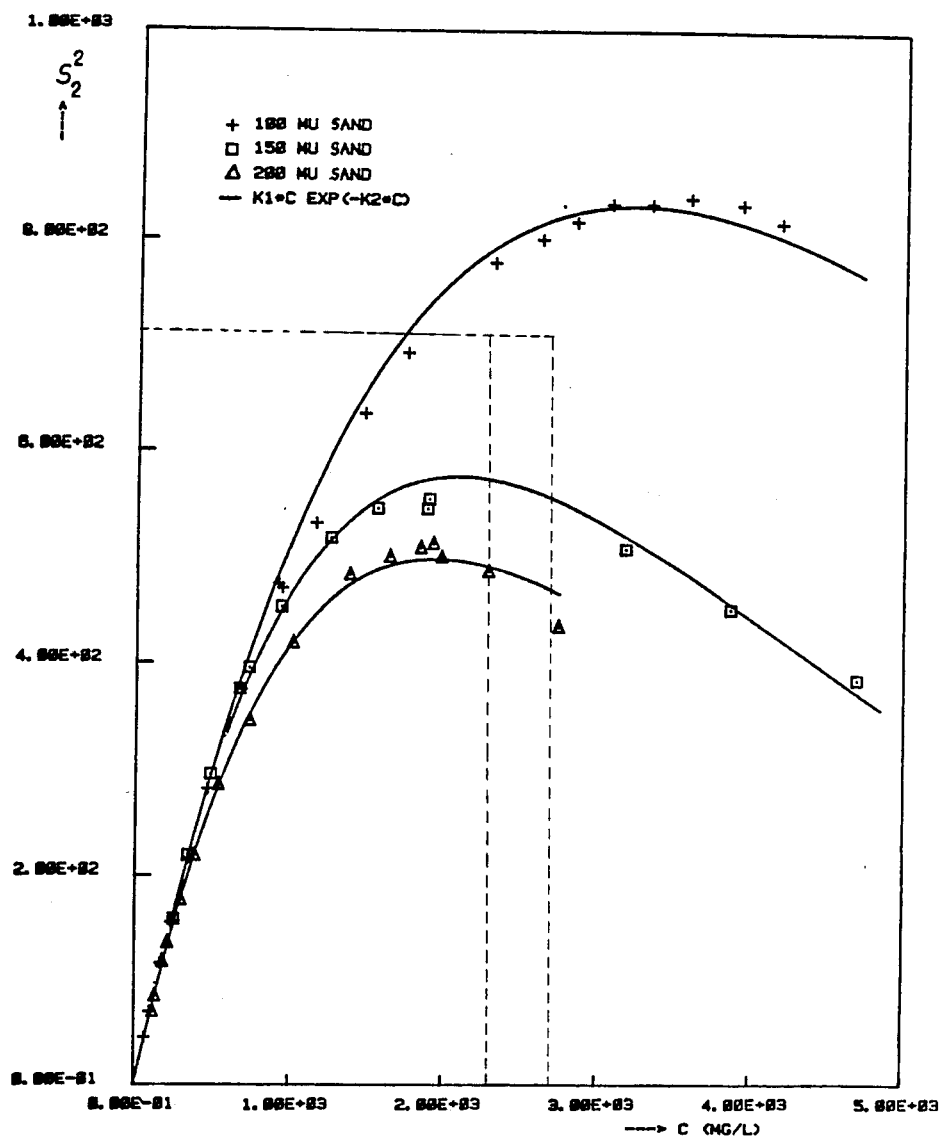
FIG. 4 illustrates in a graphical way the relation between the squared output signal of the second receiver and the particle concentration for various particle sizes.
Figure 5:
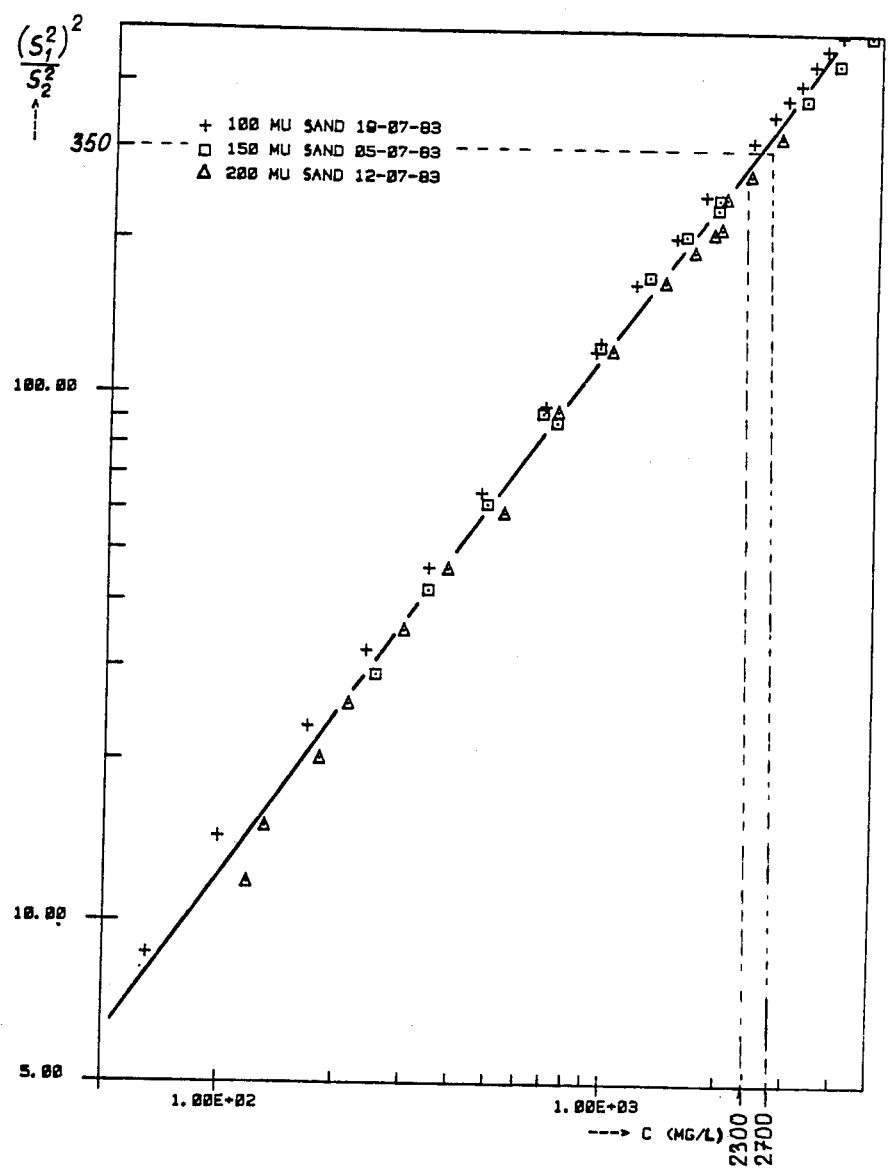
FIG. 5 illustrates in a graphical way the output signal of the measuring circuit as a function of the particle concentration.

In FIGS. 3, 4 and 5 the results, obtained with the system according to the invention, are indicated graphically. The system was used in a flowing fluid to which sand with a predetermined particle size was added. The output signals, measured and squared by means of the system according to the invention, are plotted relative to the ordinate in FIGS. 3 and 4. The concentration of the sand particles, determined by taking samples afterwards, is plotted relative to the abscissa. In each figure measurement values are indicated for sand particles having sizes of 100 μm, 150 μm and 200 μm.

In FIG. 3 the squared output signal $S_1^2$ of the first transducer T2 is illustrated. From this plot it is clear that $S_1^2$ is represented by a non-linear curve.

In FIG. 4 the squared output signal $S_2^2$ of the further receiving transducer T3 is indicated as a function of the concentration. Especially from this plot it appears that the exponential term in the formula $S_2^2$ not only causes the non-linearity of the function but furthermore makes the function ambiguous.

In FIG. 5 the output signal of the last multiplier 4 in FIG. 2, which signal should be proportional to the particle concentration, is illustrated as a function of the concentration. It appears clearly that the influence of the exponential term in the obtained formula is completely disappeared and that a linear relation is obtained between the output signal of the system and the particle concentration in the fluid.

By combining the signals $S_1^2$, $S_2^2$ and the output signal $(S_1^2)^2/S_2^2$, it is also possible to determine the particle size for concentrations above a threshold value, which in the illustrated example lies approximately at 1000 mg/l. Suppose that the output signal has a value of 350 mV; then it appears from FIG. 5, taking into account some dispersion, that the concentration is between 2300 and 2700 mg/l. If simultaneously for $S_2^2$ a value of 700 mV is measured, then it appears from FIG. 4 that after combining this 700 mV with the obtained concentration between 2300 and 2700 mg/l, the average particle size is 120 μm. If also $S_1^2$ is simultaneously measured, then the result can be verified in FIG. 3. The calculating unit 5 shown in FIG. 2a derives data relating to the particle size from the output signals of the second (2) and third (4) multipliers.

Figure 2A:
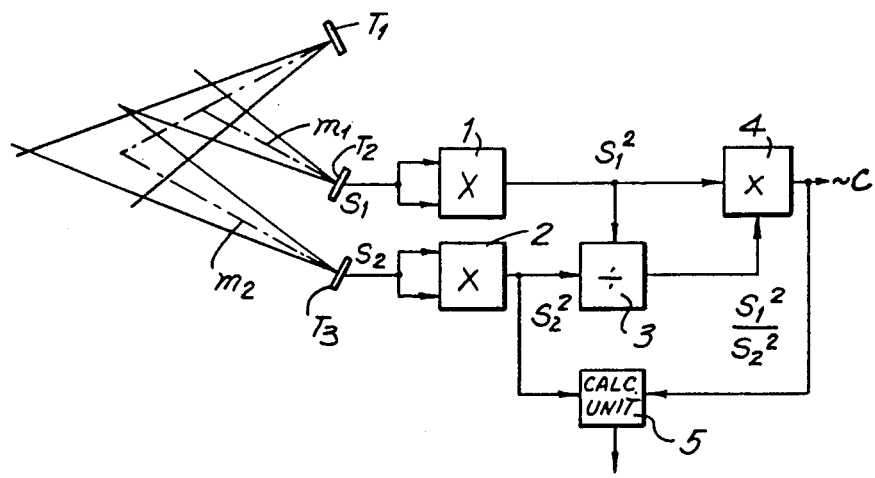
FIGS. 2a and 2b illustrate principle diagrams of the first and second preferred embodiments of the system according to the invention, in which the factor n equals 2.

Although not indicated in detail in FIG. 2a the output signals of the transducers T1, T2 and T3 are not used directly, but these signals are first supplied to a circuit in which the product signals are formed of the transmitter control signal and the amplified signals from the receiving transducers. Said product signals are in fact used as $S_1$ and $S_2$, both for the above-described concentration calculation as well as for the determination of the velocity component along the bisector of the angle between the transmission and reception beams on the basis of the above-indicated formula (1). For further details of said velocity measurement reference is made to the already earlier mentioned publication, the disclosure of which is hereby incorporated by reference.

Figure 6:
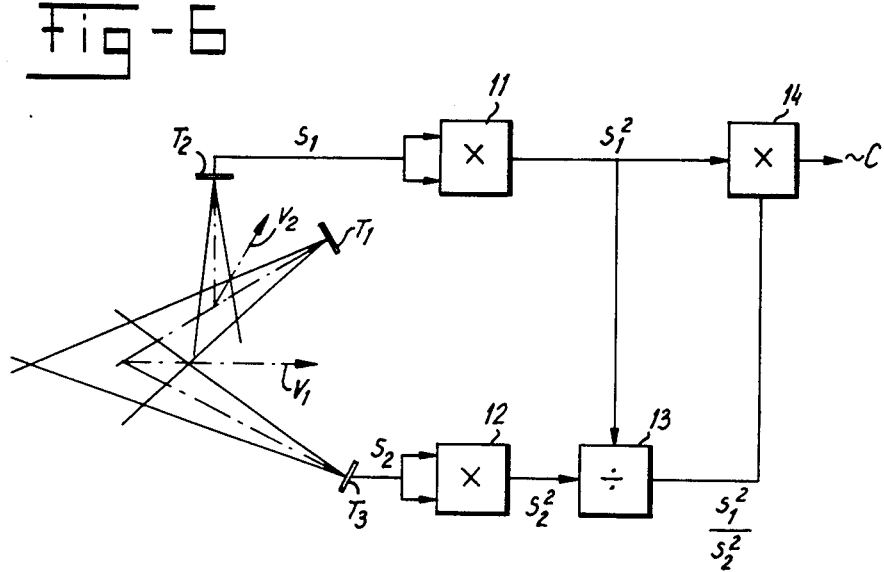
FIG. 6 illustrates a principle diagram of a third embodiment of the system according to the invention.

With the system indicated in FIG. 2a only the velocity component along the bisector of the angle between the transmission and reception directions can be determined. With said embodiment therefore only one velocity vector component is obtained. FIG. 6 illustrates a modified embodiment of the system according to the invention in which the velocity two-dimensionally, i.e. in the plane of the drawing, can be determined. In that case the measuring direction of T2 is not equal to the measuring direction of T3. However, the requirement that the length of the path $m_1$ be half the length of the path $m_2$ should be fulfilled. The components 11, 12, 13 and 14 have functions corresponding to the functions of the components 1, 2, 3 and 4 in FIG. 2. The output signal of the multiplier 14 therefore corresponds to the output signal of multiplier 4. It will be clear that with the circuit of FIG. 6 not only the velocity component $v_1$ can be measured but also the velocity component $v_2$. By combining both components the velocity component in the plane of the drawing can be obtained.

Figure 7:
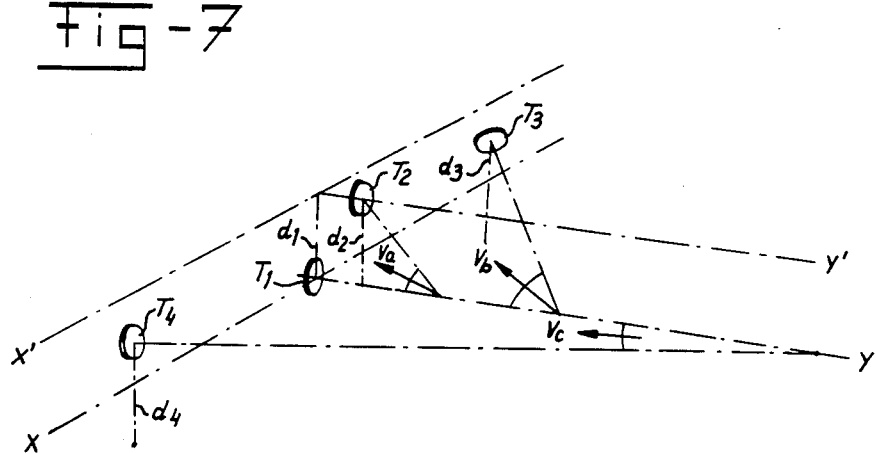
FIG. 7 illustrates a principle diagram of a fourth embodiment of a system according to the invention.

FIG. 7 illustrates in a very schematical way an embodiment of the system according to the invention, comprising a transmitting transducer T1 and three receiving transducers T2, T3 and T4. The transmitting transducer T1 is positioned at the intersection of the coordinate axes X and Y and transmits a beam of electro-acoustical energy along the Y-axis. The receiving transducers are positioned such that the sound propagation path between T1 and T2 is half the length of the sound propagation path between T1 and T3. The length of said last-mentioned path is in turn half the length of the propagation path between T1 and T4. Furthermore the receiving transducers are in this embodiment positioned in a plane through the coordinate axes X' and Y', which plane is positioned at a distance $d_1$ above the plane through axes X and Y. Therefore the various distances d in FIG. 7 fulfil the expression $d_1=d_2=d_3=d_4$. By means of this configuration it is possible to measure three different directed spatial velocity components $v_a$, $v_b$ and $v_c$ from which the three-dimensional velocity vector can be determined. If this configuration is used for measuring the transport of particles in a fluid, whereby the principal direction of movement of the particles is in the plane through axes X and Y, then a further advantage of this configuration is that the positioning of the receiving transducers in principle does not disturb the hydrodynamical flow pattern because these transducers are so to speak "elevated" out of the measuring plane. Preferably the distances $d_2$, $d_3$ and $d_4$ are selected equal to each other because of an eventual vertical concentration gradient between the measuring plane and the plane through axes X' and Y', which gradient now for each combination of transmitting transducer and receiving transducer has the same influence.

In the above-discussed embodiments of the system according to the invention in all cases different measuring volumes are used, one for each receiving transducer. In case one tries to eliminate possible problems in relation to an eventual concentration gradient, then for instance the embodiment illustrated in FIG. 8 can be used.

Figure 8:
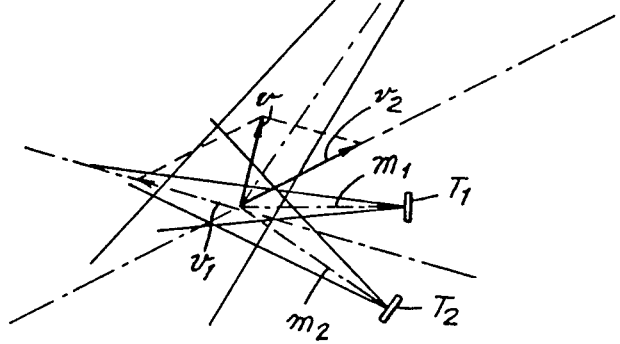
FIG. 8 illustrates a principle diagram of a fifth embodiment of a system according to the invention.

In FIG. 8 the three transducers are each directed to the same measuring volume V. Also in this case it applies for the sound propagation path that $n(m_1+m_2)=m_1+m_3$, especially that $m_3=m_1+2m_2$ for $n=2$.

As will be clear from the above description it is now possible with this configuration to measure the concentration C without any influence of an eventual concentration gradient. Also the velocity in the plane of the drawing can be determined with this configuration. A similar solution is of course applicable to the embodiment described with reference to FIG. 7.

Figure 2B:
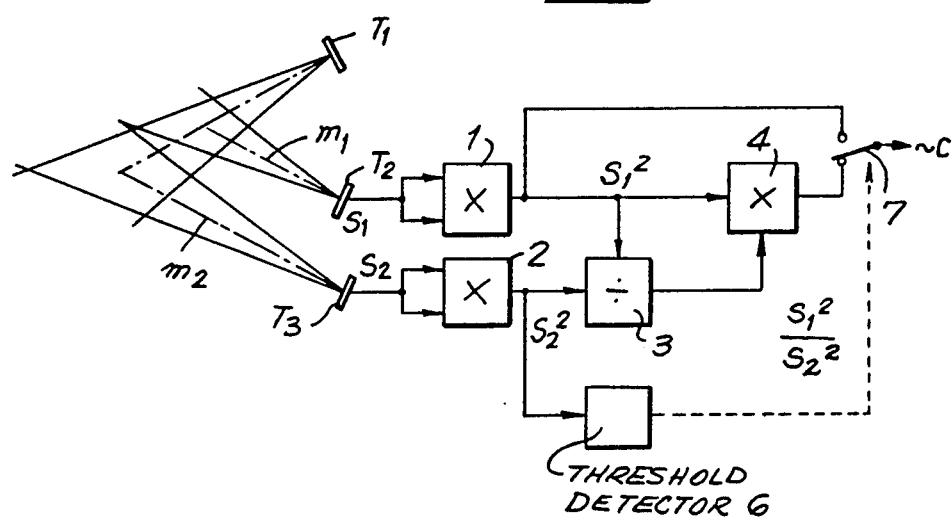

As already discussed with reference to FIG. 2 the division in the measuring circuit should be carried out by a divider 3. If very small concentrations are measured, then also correspondingly small signals are obtained at the outputs of the receiving transducers. Such small signals could result in problems for the division in the divider 3. As appears furthermore from FIGS. 3 and 4, the influence of the exponential term becomes significant only if relatively strong signals are involved. Therefore it might be preferable to insert a threshold detector between the measuring circuit and at least one of the receiving transducers, which detector provides a signal in case the signal level at the output of the transducer decreases below a predetermined value. Said signal can, for instance, be used to supply the output signal of the multiplier 1 instead of the output signal of the multiplier 4 to the output of the measuring circuit, as shown in FIG. 2b.

In addition to problems in relation to very small signals, problems can also appear in relation to the desired range of concentration values. A multiplier with a usable voltage range of 10 mV to 10 V at the output allows, for instance, a maximum dynamic variation of 30:1 for the input signals. That is just sufficient for a concentration range of 10 to 10.000 mg/l. However, the demands made upon the analog components of the measuring circuit can be very heavy and will sometimes require a circuit which is not realizable in practice. To solve this problem it is preferred to realize the measuring circuit for the larger part in a digital form.

Figure 9:
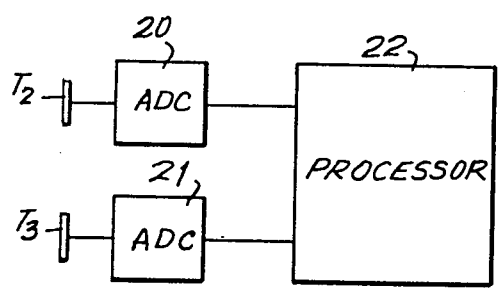
FIG. 9 illustrates a modified measuring circuit.

FIG. 9 illustrates a practical embodiment of a measuring circuit in which a digital processor is used. The output signals of the transducers T2 and T3 are in the A/D converters (ADCs) 20 and 21 periodically converted into digital values which, in a similar way as is described with reference to FIG. 2a, are used in the processor 22 to provide, by means of multiplying and dividing, a digital output signal proportional to the concentration.

It is remarked that there are at this moment processors with built-in A/D convertors available on the market, for instance, the INTEL 2920, which is well suited for application in a measuring circuit of this type.

Although in the above description of the various embodiments reference is made to the use of acoustical waves, it also possible to realize similar systems functioning with light waves. Such systems can, for instance, be used in situations in which the fluid is sufficiently light transparent. If an incandescent lamp is used then it is only possible to determine the concentration of the particles. Application of a laser light source, however, provides the possibility also to determine the velocity of the particles.

It is furthermore possible to apply high-frequency electromagnetic waves, for instance, in the radar range. In that case the system can be used, for instance, for meteorological applications, environmental pollution measuring systems, etc.

I claim:

1. In a system for measuring the concentration of objects contained in a fluid, comprising a transmitter for transmitting a wave beam in the direction of a measuring volume in the fluid under the control of an electrical control signal and a first receiver receiving, within a reception beam, waves scattered by the objects in said measuring volume and supplying a corresponding first electrical reception signal, whereby the measuring volume is determined by the intersection of the transmission beam and the reception beam, and a measuring apparatus to which the control signal of the transmitter and the first reception signal of the first receiver are supplied, the improvement wherein the system comprises a second receiver which receives scattered waves from a second measuring volume, determined by the intersection of the transmission beam and the reception beam of the second receiver, and supplies a thereto corresponding second reception signal to the measuring apparatus, whereby the wave propagation path between the transmitter and the second receiver is equal to n times the wave propagation path between the transmitter and the first receiver, where n is an integer, and the measuring apparatus comprises means for forming an output signal which can be expressed as the first reception signal raised to the n-th power, the result thereof being divided by the second reception signal, said output signal at the output of said measuring apparatus representing the concentration of objects contained in the fluid.

2. The system according to claim 1, wherein the system comprises a plurality of receivers each receiving respectively scattered waves from a corresponding number of measuring volumes within the transmission beam, in each case determined by the intersection of the transmission beam and the respective reception beam, whereby the length of the wave propagation path between the transmitter and at least one of the receivers is equal to n times the length of the propagation path between the transmitter and another receiver, whereby n is a value larger than 1.

3. The system acording to claim 2, wherein n is equal to 2.

4. The system according to claim 3, wherein the measuring apparatus comprises first and second multipliers in which the square of the output signals of the first and second receivers are formed, a divider in which the output signal of the first multiplier is divided by the output signal of the second multiplier, and a third multiplier in which the output signal of the first multiplier is multiplied by the output signal of said divider, which third multiplier supplies the output signal of the system, said output signal being proportional to the concentration of said objects in the fluid.

5. The system according to claim 4, wherein the measuring apparatus comprises a threshold circuit supplying a signal to switching means through which the output signal of the first multiplier is supplied to the output of the measuring apparatus instead of the output signal of the third multiplier in case the output signal of the second multiplier remains below a predetermined threshold value.

6. The system according to claim 4, wherein a calculating unit is added to the measuring apparatus to derive data relating to the object size out of the signals of the third and second multipliers.

7. The system according to claim 1, wherein one single measuring volume is used as the intersection of the transmission beam and all of the reception beams.

8. The system according to claim 1, wherein the plane determined by the transmission direction of the transmitter and the reception direction of the first receiver does not coincide with the plane determined by the transmission direction of the transmitter and the reception direction of the second receiver.

9. The system according to claim 1, wherein the measuring volume or measuring volumes is (are) in general determined by a horizontal plane.

10. The system according to claim 1, wherein the transmitter is a transmitting electro-acoustical transducer and each receiver is a receiving electro-acoustical transducer.

11. The system according to claim 1, wherein the transmitter comprises a light source and each receiver comprises an opto-electrical converter.

12. The system according to claim 11, wherein the transmitter comprises a laser source.

13. The system according to claim 1, wherein the transmitter comprises a radar transmitter and each receiver comprises a radar receiver.

14. The system according to claim 1, wherein the first reception signal is converted into a first digital signal by an A/D converter, the second reception signal is converter into a second digital signal by an A/D converter, and the measuring apparatus is embodied as a digital processor receiving said first and second digital signals, said digital processor being programmed to output a digital output signal representing the concentration of objects in the fluid, said digital output signal being obtained by raising the first digital signal to the n-th power and dividing the resulting value by the second digital signal.

* * * * *